United States Patent [19]

Mulieri et al.

[11] Patent Number: 5,162,374

[45] Date of Patent: Nov. 10, 1992

[54] METHOD FOR REVERSIBLY ARRESTING MUSCLE ACTIVITY

[75] Inventors: Louis A. Mulieri, Hinesburg, Vt.; Gerd Hasenfuss, Wald-Kirch, Fed. Rep. of Germany; Norman R. Alpert, Shelburne, Vt.

[73] Assignee: The University of Vermont and State Agricultural College, Burlington, Vt.

[21] Appl. No.: 714,333

[22] Filed: Jun. 12, 1991

Related U.S. Application Data

[63] Continuation of Ser. No. 430,614, Nov. 1, 1989, abandoned.

[51] Int. Cl.$^5$ .............................................. A61K 31/15
[52] U.S. Cl. ..................................... 514/640; 514/906
[58] Field of Search ............................. 514/640, 906

[56] References Cited

PUBLICATIONS

Elz, J. S. et al., Labratory Investigation 58(6): 653-659 (1988).
Williamson, Jr., Circulation 53 (3 Suppl 1): p. 3 (Abstract only) (1976).
Edery, H., Br. J. Pharmacol. 14:317-322 (1959).
Horiuti, K. et al., J. Muscle Res. Cell Motil. 9:156-164 (1988).
Higuchi, H. et al., J. Biochem. 105:638-643 (1989).
Mulieri, L. A. et al., Biophys. J. 45:47a (1984).
Wiggins, J. R. et al., J. Pharmacol. Expl. Therapeut. 212: 217-224 (1980).
Li, T. et al., Fed. Proceedings 43:768, Abstract No. 2826 (1984).
Wislicki, L., Arch. Int. Pharmacodyn. 129:1-19 (1960).
Li, T. et al., J. Pharmacol. Expl. Therapeut. 232:688-695 (1985).
Warren, T. B. et al, Biophys. J. 47:Abstract 295A (1985).
Loiselle, D. S. et al., J. Mol. Cell. Cardiol. 18:Abstract 271 (1986).
Sada, H. et al., Fed. Proc. 45:770 (1986).
Packer, C. S. et al., Pflugers Arch. 412:659 (1988).
Naylor et al., in Diastolic Relaxation of the Heart, Grossman and Lorell editors, Martin Nijhoff Publishing, Boston, Mass. (1988).
West, J. M. et al., Pflugers Arch. Eur. J. Physiol. 413: 546-552 (1989).
Blanchard et al., Biophys. J. 45:48a (1984).

Primary Examiner—Richard L. Raymond
Assistant Examiner—G. Hollinden
Attorney, Agent, or Firm—Lahive & Cockfield

[57] ABSTRACT

Muscle activity can be reversibly arrested by administering a reagent, such as 2,3-butanedione monoxime (BDM), which selectively blocks the interaction of the contractile proteins actin and myosin. Muscle such as the heart is contacted with the reagent to arrest activity and, after surgery or transplantation, the reagent is removed from the muscle to restore muscle activity. The preferred reagent BDM has the following structure:

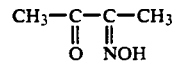

8 Claims, No Drawings

METHOD FOR REVERSIBLY ARRESTING MUSCLE ACTIVITY

GOVERNMENT SUPPORT

Work described herein was supported by National Institutes of Health Grant PHS 28001-04/P1.

This application is a continuation of application Ser. No. 07/430,614, filed Nov. 1, 1989, now abandoned.

BACKGROUND

Cardioplegia is an elective stopping of cardiac activity temporarily by injection of chemicals, selective hypothermia, or electrical stimuli. Presently, the most widely employed method of cardioplegia is by injection of potassium chloride (KCl). KCl causes reversible arrest of the beating and blood pumping activities of the heart. In addition to this desired effect, KCl injection has a number of undersirable side effects. For example, KCl treatment induces a transient state of sustained muscular contracture which, in turn, results in the rapid depletion of cellular energy stores (ATP and PCr). As a consequence, the permissible duration of cardiac arrest is shortened by this accelerated expenditure of cellular energy.

Following the transient contracture and rapid depletion of energy stores, there is a further, gradual, depletion of energy stores due to basal metabolism. When the later causes energy stores to fall sufficiently low, the muscle cells can no longer keep calcium ions pumped out of the myoplasm. This triggers a renewed activation of muscular contraction which rapidly further reduces the energy stores and leads to cell death and rigor mortis. Additionally, surgery performed on muscle arrested but still capable of undergoing contraction can result in contracture-induced self destruction. Self-destruction results when the mechanical forces produced by one cell during contracture are transmitted to adjacent, previously undamaged cells causing them to be damaged and to go into contracture. In this way, the original damage can be propogated through the bulk of the muscle.

Among the other KCl induced side effect are depolarization, loss of cellular excitability, and major shifts in cellular electrolyte balance. Such side effects render the electrocardiogram useless as a diagnostic aid during the period of cardioplegia.

A compound which could induce cardioplegia without these undesirable side effects would be useful as a cardioplegic agent.

SUMMARY OF THE INVENTION

This invention pertains to methods and compositions for arresting muscle activity comprising contacting muscular tissue with a diffusible, non-toxic chemical agent which selectively and reversibly blocks the interaction of the contractile proteins actin and myosin thereby eliminating contraction and its associated self-destructive potential and the rapid consumption of energy. In a preferred embodiment, the muscular tissue is myocardium and the chemical agent is 2,3-butanedione monoxime.

DETAILED DESCRIPTION OF THE INVENTION

The compounds of this invention reversibly arrest muscle contraction by blocking the interaction of the actin and myosin contractile proteins. Muscle tissue which is contacted with effective amounts of these compounds is induced to assume a relaxed state of non-contracture. In this state, the contractile proteins will not produce force or motion even if calcium ions enter to myoplasm as a result of cell injury induced by cutting during surgery or by contracture of adjacent cells or by depletion of energy stores due to prolonged oxygen lack.

The specific blockage of the interaction between actin and myosin is accomplished by contacting a muscle tissue with an effective amount of the compounds of this invention. The specific blockage can be regional (i.e. affecting only a portion of a particular muscle), or it can effect an entire muscle or muscle group depending upon the extent of the contact between the muscle tissue and the compound. For example, if one end of an elongate muscle is immersed in a solution containing a compound of this invention, the interaction of actin and myosin in that portion of the muscle which is immersed would be blocked whereas that portion of the muscle not brought into contact with the compound would retain the ability to contract in response to an appropriate signal.

This chemically induced blockage of the actin and myosin interaction is reversible. The diffusible compound responsible for the blockage is simply allowed to diffuse away from the filaments thereby restoring the contractile properties to the thick and thin filaments.

A preferred embodiment of the invention pertains to cardioplegia which is an elective, temporary stopping of cardiac activity. Cardioplegic compositions enable the stoppage of cardiac activity temporarily and reversibly. This reversible arrest of myocardial contraction is required for successful heart surgery and also facilitates the preservation of a heart, for example, during transport prior to a heart transplant operation.

The preferred active chemical agent of the preferred cardioplegic solution is 2,3-butanedione monoxime (BDM) or homologues thereof. Homologues, as that term is used herein, refers to compounds (e.g. structurally related compounds) which exhibit similar cardioplegic properties when administered to an organism. A preferred concentration range for BDM in the cardioplegic solutions is from 10–40 mM. The BDM solution can be prepared in any physiologically compatible buffer. One such buffer is Krebs-Ringer which contains physiologically acceptable levels of $Na^+$, $K^+$, $CL^-$, $SO_4^{2-}$, $Ca^{2+}$ glucose. A preferred cadioplegic composition is given in the Exemplification. As an optional ingredient insulin (e.g., 10 IU per liter) can be included. As shown in the Exemplification, the addition of insulin when combined with an increase in the glucose concentration (to 11.2 mM) increased yielded stable performance in the assay to a level of 80–100%.

The cardioplegic solutions are administered by contacting the solution with the myocardium. For example, a cardioplegic solution equilibrated with a 95% $O_2$—$CO_2$ gas mixture can be introduced by pressure perfusing the coronary circulation. Cardioplegia can also be induced by immersing the heart or a region of the heart in a cardioplegic solution. This immersion perfusion also provides a convenient method for transferring a heart from a donor to a recipient prior to a transplant operation. The cardioplegia (or other muscle stoppage) can be reversed by removing the solution, preferably at 30° C.

BDM induced cardioplegia blocks muscle contraction in a relaxation state without causing sustained contraction which would mechanically damage muscle cells and seriously deplete the cellular energy stores (ATP and PCr) shortening the permissible duration of cardiac arrest. Muscle tissue is thereby protected from contracture-induced self destruction caused by cutting or depletion of energy stores during surgery. The most probable mechanism by which BDM prevents cutting injury is by reducing the contracture that results from cutting cell membranes. This reduction diminishes the tendency of injured cells to tear themselves apart during the membrane's self-healing period. BDM reduces the contractures because it decreases the sensitivity of the contractile proteins to calcium ions and exerts a direct inhibitory effect on cross-bridge interaction.

In addition, another advantage of the compositions and methods of this cardioplegic embodiment is that they do not cause a shift in electrolyte balance nor do they create a hazard of potassium ion leakage into systemic circulation. Also, in contrast to prior art methods, the compositions of this invention do not block cellular excitability thereby preserving the electrocardiograph for use as a diagnostic aid (oxygenation status, etc.) during the period of cardiac arrest. The electrocardiograph is an instrument for recording the potential of the electrical currents that traverse the heart and initiate its contraction. Enabling its use during open heart surgery is a significant advance over the prior art. Ye another advantage of the present invention for use as a cardioplegic agent is the property of the BDM solution to induce relaxation of coronary artery musculature which prevents blockage of coronary circulation during coronary perfusion.

While in a state of BDM-induced cardioplegia, a heart continues to use cellular energy to maintain basal metabolic activities. A limitation associated with BDM-induced cardioplegia (as with previously known methods) is that the myocardium continues to utilize stored cellular energy to meet its basal metabolic needs. This places constraints upon the period of time for which a heart can be maintained in a cardioplegic state. This limitation could be minimized by perfusing the coronary circulation within oxygenated BDM cardioplegia solution.

To reverse BDM induced cardioplegia, the heart is perfused within a physiologically compatible buffer without BDM for a period of time sufficient to remove the critical concentrations of BDM from the cardic tissue. Preferably the BDM solution is washed out and the myocardium equilibrated with physiologically compatible buffer at 30° C.

Other uses for the invention include the preservation of biopsy tissue (for example, myocardium) in a living state for purposes of analysis at a later time. The invention also facilitates the relaxation and protection of blood vessel smooth muscle during dissection and during shipment by contacting the muscle with the composition. Coronary vasculature may also be relaxed, in situ, during angioplasty to avoid vasospasm by infusion of a solution of the invention (e.g., BDM containing cardioplegic solution) via a catheter. Skeletal muscle may also be relaxed without impairing neuromuscular transmission or excitability.

The invention is illustrated further by the following exemplification.

EXEMPLIFICATION

Materials and Methods

In preliminary experiments with normally dissected rabbit right ventricular papillary muscles, increasing quantities of BDM were added to normal Krebs' solution until visual signs ($\times 10$ magnification) of the contracture response to cutting or pinching the tissue were minimized. Although the protective effect of BDM seemed to saturate at a concentration of 20–25 mM, 30 was used because in muscle strips cut from do left ventricular papillary muscles, spontaneous peristalic contractions of sarcomeres ($\times 400$ bright field microscopy) were observed unless the higher dose was used. The "protective" BDM-Krebs solution contains (mM) BDM 30, $Na^+$152, $K^+$3.6, $Cl^-$135, $HCO_3^-$25, $Mg^{2+}$0.6, $H_2PO_4^-$0.6, $Ca^{2+}$2.5, and glucose 5.6. In later experiments, it was found that doubling the glucose concentration to 11.2 mM and adding 10 IU insulin per liter of solution increased the percentage of strip preparations that gave stable performance to 80–100%.

The reversibility of pretreatment with BDM on conventionally dissected right ventricular papillary muscles from rabbit hearts that were not pretreated with BDM was measured. Isometric twitch tension was measured before soaking the muscles in 30 mM BDM-Krebs-Ringer solution for 30–60 minutes. Twitch tension was measured again after washout of the protective solution and found to decline by $2.5\pm2.32\%$. A paired t test indicated that the reversal values were not significantly different from the control values ($p>0.05$, $n=8$).

The degree of protection by the BDM solution against the injury of cutting the base of the muscle away from the ventricular wall in conventionally prepared right ventricular papillary muscles was also measured. Isometric twitch tension (0.3 Hz, pretreated by soaking in 30 mM BDM-Krebs solution for 30 minutes before excising the muscle was $2.85\pm0.26$ g/mm$^2$ ($n=12$), which was 46% greater ($p-<0.05$) than the value obtained ($1.95\pm0.27$ g/mm$^2$, $n=5$) from muscles prepared in the conventional way without pretreatment of the heart.

The possibility that the protective action of BDM is achieved through an osmotic rather than a specific effect was assessed by determining experimentally whether the cells were impermeable to BDM. The effect of adding 163 mM BDM to the Krebs-Ringer solution on muscle cross-sectional area was compared with the effect of adding the same amount of mannitol to give 1.5 times normal osmotic strength. Average cross-sectional area was determined by optical measurement ($\times 50$ magnification) of four diameters at each of four places (a total of 16) along the length of the muscle. In five preparations (three human and two rabbit), addition of 163 mM mannitol caused a $10.1\pm1.2\%$ ($p<0.05$) decrease in cross-sectional area whereas addition of the same quantity of BDM caused a slight ($5.2\pm1.1\%$, $p=NS$) increase in cross-sectional area. This shows that the BDM used in the protective solution (30 mM) was permeable and would exert negligible osmotic effects on the myocardial cells.

Human papillary muscle tissue was obtained from mitral valve replacement surgery in three cases of severe mitral regurgitation, in one case of mitral stenosis with combined moderate mitral regurgitation, and in one case of combined aortic and mitral regurgitation. Immediately after excision of a portion of the tendinous end of the anterior papillary muscle, the tissue was submerged in preoxygenated (95% $O_2$–5% $CO_2$) BDM-Krebs-Ringer solution (21° C.). After 30 minutes, the tissue was transferred to the dissection chamber containing the same solution and mounted between clamps. Muscle strips ($0.49\pm0.16$ mm$^2$ cross section, $6.8\pm1.4$ mm length, n=11) were cut along the fiber direction by means of scissors (6-mm blade) under a ×7–10 binocular microscope. Silk ligatures containing platinum wires were attached to the muscles to facilitate end-to-end stimulation and connection to the isometric force gauge. After this, the muscle strips were either used immediately (60 minutes after excision) or stored in continuously oxygenated BDM-Krebs-Ringer solution for later experimentation. To perform force and heat measurements, the muscle strip was mounted in contact with the active region of a thermopile and connected to the force gauge. The muscle and thermopile were then submerged in normal Krebs-Ringer solution at 21° C. which washed out the BDM solution. Stimulation was begun at intervals of 6 seconds, 20% above threshold. All--or-none responses were obtained in each preparation and twitch force increased during 60 minutes until a stable force value was reached. In later experiments, it was found that raising the temperature to 30° C. during BDM washout and equilibration improved muscle recovery considerably. After another 30–60 minutes, the muscle was stretched to optimum length at which maximum twitch force was reached. Thereafter, heat and mechanical measurements were performed and analyzed as previously described. Mechanical measurements were performed at 21° C. (n=11), 30° C. (n=5), and 37° C. (n=3). Force-frequency relations were measured at 24° C., 30° C., and 37° C. in two muscle strips preparations. Complete time-course heat records were corrected for heat loss by the Hill method. In a few preparations, myocyte orientation and sarcomere length were assessed by using x400 bright field microscopy to confirm that cell orientation was parallel to the longitudinal axis of the muscle strips. Resting sarcomere lengths of $2.3-2.4 \times 10^{-6}$ m were observed at optimum length. Cross sections were estimated from the blotted weight and length of the portion of muscle strip lying between the two silk ligatures assuming unity density. Values are given as means $\pm$SD.

Results

Records at optimum length from a human myocardium preparation were determined. The heat record exhibits expected behavior in that it has a rapidly rising phase (initial heat) which ends near the time of complete relaxation of force. This phase is followed by a slow phase of heat evolution attributable to recovery heat. Of particular interest is the lack of time delay in onset of heat,, evolution since presence of as little as $50 \times 10^{-6}$ (6% of muscle diameter) of dead tissue would cause the rise time to increase from 20 to 470 msec.

In the human myocardium, average peak twitch tension at 21° C. was $2.02\pm1.33$ g/mm$^2$, which ranged from 0.67 to 5.5 g/mm$^2$ (n=11). One preparation was stored in BDM-Krebs-Ringer for 20 hours before use and had a peak twitch tension of 1.85 g/mm$^2$. When the temperature was increased above 21° C., peak twitch tension increased continuously (by 38%) up to about 28° C.; above this temperature, peak twitch tension decreased so that at 37° C. (n=3) it was lower than the 21° C. value by 47%.

The force-frequency relations at 24° C., 30° C., and 37° C. were also determined. At 37° C., total twitch duration decreased as frequency increased so that it remained shorter than stimulus interval up to 2-Hz stimulation rate.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for reversibly arresting human cardiac muscle activity comprising the steps of:
   a. contacting cardiac muscle tissue with an effective amount of a diffusible, non-toxic chemical agent which selectively and reversibly blocks the interaction of the contractile proteins actin and myosin thereby eliminating contraction and its associated consumption of energy; and
   b. following a selected amount of time, removing an amount of the chemical agent form contact with the cardiac muscle tissue sufficient to restore the muscle activity.

2. The method of claim 1, wherein the chemical agent is 2,3-Butanedione monoxime or homologues thereof.

3. A method of reversible cardioplegia for heart transplantation, comprising the steps of:
   a. contacting a human donor heart with an effective cardioplegic amount of 2,3-Butanedione monoxime;
   b. maintaining the heart in contact with the 2,3-Butanedione monoxime; and
   c. surgically introducing the heart into a recipient patient and removing the 2,3-Butanedione monoxime from the heart to reverse the cardioplegia.

4. The method of claim 3, wherein the 2,3-butanedione monoxime is introduced into coronary circulation to induce the cardioplegia.

5. A method of claim 3, wherein the myocardium is immersed into a physiologically acceptable solution comprising an effective cardioplegic amount of 2,3-butanedione monoxime or a homologue thereof.

6. The method of claim 3, wherein 2,3-butanedione is in a physiologically acceptable solution.

7. A method of claim 6, wherein the solution comprises $Na^+$, $K^+$, $Cl^-$, $HCO_3^-$, $Mg^{2+}$, $H_2PO^{4-}SO_4^{2-}-Ca^{2+}$ and glucose.

8. A method of claim 3, further comprising reversing the cardioplegia by removing the 2,3-butanedione from contact with the myocardium.

* * * * *